(12) United States Patent
Allex et al.

(10) Patent No.: US 6,223,128 B1
(45) Date of Patent: Apr. 24, 2001

(54) DNA SEQUENCE ASSEMBLY SYSTEM

(75) Inventors: Carolyn F. Allex, Verona; Jude W Shavlik; Frederick R. Blattner, both of Madison, all of WI (US)

(73) Assignee: DNStar, Inc., Madison, WI (US)

( * ) Notice: Subject to any disclaimer, the term of this patent is extended or adjusted under 35 U.S.C. 154(b) by 0 days.

(21) Appl. No.: 09/106,370

(22) Filed: Jun. 29, 1998

(51) Int. Cl.$^7$ .......................... G01N 33/48; G01N 33/50; G06F 19/00; C12Q 1/68
(52) U.S. Cl. .................. 702/20; 702/19; 435/6; 435/501
(58) Field of Search ................. 435/6, 501; 707/104, 707/10; 702/20

(56) References Cited

PUBLICATIONS

Drmanac R et al, "DNA sequence determination by hybridization: A strageggy for efficient large–scale sequencing", Science, vol. 260, Jun. 11, 1993, pp. 1649–1652.*

Bonfield et al., "A New DNA Sequence Assembly Program", *Nucleic Acid Res.* 23(24):4992–4999 (1995).

Boysen et al., "Analysis of the 1.1–Mb Human α/δ T–Cell Receptor Locus with Bacterial Artificial Chromosome Clones", *Genome Research* 7:330–338 (1997).

Green, P., "Against a Whole–Genome Shotgun", *Genome Research* 7:410–417 (1997).

Green, P., "Genome Sequence Assembly", *Plenary Speaker Abstracts; Plenary Session* 6, p. 15.

Huang, X., "An Improved Sequence Assembly Program", *Genomics* 33:21–31 (1996).

Jain and Myers, "Algorithms for Computing and Integrating Physical Maps Using Unique Probes", *J. of Computational Biology* 4(4):449–466 (1997).

Lawrence et al., "The Genome Reconstruction Manager: A Software Environment for Supporting High–Throughput DNA Sequencing", *Genomics* 23:192–201 (1994).

Parsons and Johnson, "DNA Sequence Assembly and Genetic Algorithms New Results and Puzzling Insights", *ISMB*–95 published by AAAI Press (1995).

Smith et al., "High Throughout DNA Sequencing Using an Automated Electrophoresis Analysis System and a Novel Sequence Assembly Program", *Bio Techniques* 14(6):1014–1018 (1993).

Studier, F., "A Strategy for High–Volume Sequencing of Cosmid DNAs: Random and Directed Priming with a Library of Oligonucleotides", *Proc. Natl. Acad. Sci.* 86:6917–6921 (1989).

Sutton et al., "TIGR Assembler: A New Tool for Assembling Large Shotgun Sequencing Projects", *Genomic Science & Tech.* 1(1):9–19 (1995).

Swindell and Plasterer, "Cotig Assembly", *Methods in Molecular Biology*, vol. 70 *Sequence Data Analysis Guidebook*, edited by S.R. Swindel, p. 75–89 (1997).

Venter et al., "A New Strategy for Genome Seqeuncing", *Nature* 381:364–365 (1996).

Sequencing Information Home page, "Alewife Assembler", Web page, undated.

Weber, J. and E.W. Meyers, "Human Whole–Genome Shotgun Sequencing", *Genome Research* 7:401–409 (1997).

* cited by examiner

*Primary Examiner*—John S. Brusca
*Assistant Examiner*—Stephen Siu
(74) *Attorney, Agent, or Firm*—Quarles & Brady LLP

(57) ABSTRACT

A computerized method is described for assembling DNA sequence determined for small DNA fragments, called fragment reads, into larger fragments of DNA sequence called contigs. The method used makes a table of occurrences or counts for each mer appearing in any of the fragment reads and then picks from among those mers specific mers to use as mer tags. Following checking, the mer tags are used to assemble fragment reads into contigs. A feature of this method is that the processing time necessary to perform this process on a computer varies linearly with the number of fragment reads rather than with the square or cube of the number of fragment reads.

19 Claims, 10 Drawing Sheets

```
GCAATGTCATATGGCAGTACACGGCGTACGTTAGGTTTCTGAGGGATTTTCGAG    2A

GCAATGTCATATGGCAGTA              2B
TATGGCAGTACACGGCGTACGT           2C
GGCGTACGTTAGGTTT                 2D
AGGTTTCTGAGGGATT                 2E
AGGTTTCTGAGGGATTTTCGAC           2F

GCAATGTCATATGGCAGTA                                        2B
        TATGGCAGTACACGGCGTACGT                             2C
                   GGCGTACGTTAGGTTT                        2D
                            AGGTTTCTGAGGGATT               2E
                            AGGTTTCTGAGGGATTTTCGAC         2F
```

CGCATGCAAAAGTGATCGGGTATCACGCACGTATTCTTAGCAGAGTTAT         3A

CGCATGCAAAAGTGATCGGGTATCACG                                3B
     AAAGTGATCGGGTATCACGCACGTATTC                      3C
            CACGCACGTATTCTTAGCAGAGTT              3D
                 GTATTCTTAGCAGAGTTATCCAACCATA      3E

CGCATGCAAA<u>AGTGATCGGGTATC</u>ACG                                3F
    AA<u>AGTGATCGGGTATC</u>ACGCACGTAT

CACGCACGT<u>ATTCTTAGCAGAGTT</u>                        3G
            GT<u>ATTCTTAGCAGAGTT</u>ATCCAACCATA

CGCATGCA<u>AAAGTG</u>ATCGGGT<u>ATCACG</u>                              3H
    <u>AAAGTG</u>ATCGGGT<u>ATCACG</u>CACGTATTC
        CACGCAC<u>GTATTC</u>TTAGC<u>AGAGTT</u>
            <u>GTATTC</u>TTAGC<u>AGAGTT</u>ATCCAACCATA

CGCATGCA<u>AAAGTG</u>ATCGGGT<u>ATCACG</u>                              3B
    <u>AAAGTG</u>ATCGGGT<u>ATCACG</u>CACXTATTC                        3C1

CACGCAC<u>GTATTC</u>TTAGC<u>AGAGTT</u>                        3D
            <u>GTATTC</u>TTAGC<u>AGAGTT</u>ATCCAACCATA                3E

FIG. 3

```
CGCATGCAAAAGTGATCGGGTATCACGCACGTATTCTTAGCAGAGTTATCCAACCATA          4A

CGCATGCAAAAGTGATCGGGTATCACGCACGTATTC                           4B
           TGCAAAAGTGATCGGGTATCACGCACGTATTCTTAGCAGAGTTATC             4C
                          CACGCACGTATTCTTAGCAGAGTTATCCAAC             4D
                             CACGTATTCTTAGCAGAGTTATCCAACCATA          4E
#Occur:1111222222222222222222233334444444443333333333333332-------

Partitions:
  Read 4B: CGCATGCAAAAG TGATCGGGTATC ACGCACGTATTC                     4F
  #Occur:  111122222222 222222222223 33344-------
```

FIG. 4

```
XXXXXXXXXXXXXXXXAAAAAAAABBBBBBBBCCCCCCCCYYYYYYYYYYYYYYYY              5A

XXXXXXXXXXXXXXXXAAAAAAAABBBBBBBB                                      5B
        AAAAAAAABBBBBBBBCCCCCCCC                                      5C
CCCCCCCCYYYYYYYYYYYYYYYY                                              5D

XXXXXXXXXXXXXXXXAAAAAAAABBBBBBBB
                AAAAAAAABBBBBBBBCCCCCCCC                              5E
                        CCCCCCCCYYYYYYYYYYYYYYYY

XXXXXXXXXXXXXXXXAAAAAAAABBBBBBBB
                AAAAAAAABBBBBBBBCCCCCCCC                              5F
                        CCCCCCCCYYYYYYYYYYYYYYYY
```

FIG. 5

AAAAAAAAAAABBBBBBBBCCCCCCCCCCCCCCCCCBBBBBBBBDDDDDDDDDDDDDDD    6A

AAAAAAAAAAA<u>BBBBBBBB</u>CCCCC    6B
A<u>BBBBBBBB</u>CCCCCCCCCCCCCCCCCBB    6C
CCCCCCCCCCCCCCC<u>BBBBBBBB</u>DDD    6D
CCCCCC<u>BBBBBBBB</u>DDDDDDDDDDDDD    6E

AAAAAAAAAAA<u>BBBBBBBB</u>CCCCC
            A<u>BBBBBBBB</u>CCCCCCCCCCCCCCCCCBB    6F
CCCCCCCCCCCCCCC<u>BBBBBBBB</u>DDDDD
        CCCCCC<u>BBBBBBBB</u>DDDDDDDDDDDDD

FIG. 6

AAAAAAAABBBBBBBCCCCCCCCCCCCCCCCCBBBBBBBBDDDDDDDEEEEEEE    7A

AAAAAAAABBBXBBBBCCCCCCCCCCCCC    7B
AAAAAAAABBBBBBBB    7C
BBBBBBBBDDDDDDD    7D
BBBBBBBBDDDDDDDEEEEEEE    7E

<u>AAAAAAAA</u>BBBXBBBBCCCCCCCCCCCCC    7F
<u>AAAAAAAA</u>BBBBBBBB

BBBBBBBB<u>DDDDDDD</u>    7G
BBBBBBBB<u>DDDDDDD</u>EEEEEEE

AAAAAAAABBBXBBBBCCCCCCCCCCCCC
AAAAAAAA<u>BBBBBBBB</u>    7H
    <u>BBBBBBBB</u>DDDDDDD
    <u>BBBBBBBB</u>DDDDDDDEEEEEEE

FIG. 7

ACCCATAGATGCGACTGGTAGACAGTGACACGATAGGCTAATTTACGGCAGCATTAAAGT   8A
ACCCATAGATGCGACTGGTAGACAGTGACACGATAGGCTAATTTGATCGATCAGTCAGCC   8B
                                           xxxxx x    x   x   xxx

FIG. 8

CGCATGCAAAAGTGATCGGGTATCACGCACGTATTCTTAGCAGAGTTATCCAACC   9A

CGCATGCAAAAGTGATCGG   9B
      AAAGTGATCGGGTATCA   9C
            CGGGTATCACGCACGTATTC   9D
                  CACGCACGTATTCTTAGCAGAGTT   9E

Contig 1:
  CGCATGCA<u>AAAGTGAT</u>CGG
        <u>AAAGTGAT</u>CGGGTATCA   9F

Contig 2:
  CGGGTATC<u>ACGCACG</u>TATTC
        <u>ACGCACG</u>TATTCTTAGCAGAGTT   9G Merged Contigs 1 and 2:
  CGCATGCAAAAGTGATCGG
        AAAGTGATC<u>GGGTATCA</u>
                C<u>GGGTATCA</u>CGCACGTATTC   9H
                            CACGCACGTATTCTTAGCAGAGTT

FIG. 9

| Index | Mer (first x bases) | 2-Bit Encoding |
|---|---|---|
| 0 | AAAAAAAA | 0000000000000000 |
| 1 | AAAAAAAG | 0000000000000001 |
| 2 | AAAAAAAT | 0000000000000010 |
| --- | --- | --- |
| 65,533 | CCCCCCCG | 1111111111111101 |
| 65,534 | CCCCCCCT | 1111111111111110 |
| 65,535 | CCCCCCCC | 1111111111111111 |

FIG. 11

| hash index (first x bases) | merList (last y bases) | | |
|---|---|---|---|
| | merRec 1 | merRec 2 | merRec 3 |
| 31,352 (GCTTGCTA) | mer GTCA<br>count 1<br>repeat false<br>merFrgList null | mer TTAC<br>count 6<br>repeat false<br>merFrgList null | mer GAAT<br>count 3<br>repeat false<br>merFrgList null |

FIG. 12 a) ctgList

| ctgListIdx | ctgFrgList | | | | |
|---|---|---|---|---|---|
| 1 | frgIdx 16<br>offset 0 | frgIdx 6<br>offset 8 | frgIdx 2<br>offset 14 | frgIdx 14<br>offset 25 | frgIdx 10<br>offset 34 |
| 2 | frgIdx 1<br>offset 0 | frgIdx 7<br>offset 9 | frgIdx 15<br>offset 19 | | |
| 3 | frgIdx 12<br>offset 0 | frgIdx 3<br>offset 6 | frgIdx 13<br>offset 17 | frgIdx 5<br>offset 33 | | b) Layout

```
Contig 1
   frgIdx   16:   TAGGCTAGGCCCCATATGC
   frgIdx    6:           GCCCCATATGCTGACGGCGCA
   frgIdx    2:                 TATGCTGACGGCGCATTTGAC
   frgIdx   14:                            CGCATTTGACCCCAAAGTC
   frgIdx   10:                                     CCCCAAAGTCCCCG Contig 2
   frgIdx    1:   GATTGGGGACCAGCACCACCTTAGC
   frgIdx    7:            CCAGCACCACCTTAGCAGGA
   frgIdx   15:                      CTTAGCAGGATTGACACGGGTA Contig 3
   frgIdx   12:   TTAGGATCGCGAGCTTA
   frgIdx    3:         TCGCGAGCTTATCCAGAGTCGACCGG
   frgIdx   13:                    TCCAGAGTCGACCGGTAGGGCTACACAAG
   frgIdx    5:                                    AGGGCTACACAAGCCT
```

FIG. 13

Fragment reads in MerfrgList for mer ACCAGACC:
1. GACCACACCGTAGTG
2. AGGATAGACCACACCGTAG
3f. AGACCACACCGTAGTGACCCACCCC  (Reverse-complemented)
3r. GGGGTGGGTCACTACGGTGTGGTCT  (Forward)

Make a new contig with fragment read 1:
1. GACCACACCGTAGTG   offset = 0

Add fragment read 2:

1.             GACCACACCGTAGTG   offset = 6
2.     AGGATAGACCACACCGTAG       offset = 0

Add fragment read 3:

GACCACACCGTAGTG                        offset = 6
AGGATAGACCACACCGTAG                                  offset = 0
     AGACCACACCGTAGTGACCCACCCC      offset = 5

FIG. 14

| Complexity | Step |
|---|---|
| constant | 1. Initialize all variables and structures |
| n | 2. Add fragment read information to fragment list |
| n | 3. Count occurrences of mers in all fragment reads |
| n | 4. For each read, choose mer tags using mer counts |
| n | 5. For each read, if a mer is chosen as a tag for any read, choose it as a tag for the current read |
| n | 6. Make contigs |

SEQUENCE LISTING

```
<160> NUMBER OF SEQ ID NOS: 11

<210> SEQ ID NO 1
<211> LENGTH: 54
<212> TYPE: DNA
<213> ORGANISM: Artificial Sequence
<220> FEATURE:
<223> OTHER INFORMATION: Description of Artificial Sequence: Nonsense
      sequence

<400> SEQUENCE: 1
gcaatgtcat atggcagtac acggcgtacg ttaggtttct gagggatttt cgag            54

<210> SEQ ID NO 2
<211> LENGTH: 58
<212> TYPE: DNA
<213> ORGANISM: Artificial Sequence
<220> FEATURE:
<223> OTHER INFORMATION: Description of Artificial Sequence: Nonsense
      sequence

<400> SEQUENCE: 2
cgcatgcaaa agtgatcggg tatcacgcac gtattcttag cagagttatc caaccata       58

<210> SEQ ID NO 3
<211> LENGTH: 60
<212> TYPE: DNA
<213> ORGANISM: Artificial Sequence
<220> FEATURE:
<223> OTHER INFORMATION: Description of Artificial Sequence: Nonsense
      sequence

<400> SEQUENCE: 3
acccatagat gcgactggta gacagtgaca cgataggcta atttacggca gcattaaagt     60

<210> SEQ ID NO 4
<211> LENGTH: 60
<212> TYPE: DNA
<213> ORGANISM: Artificial Sequence
<220> FEATURE:
<223> OTHER INFORMATION: Description of Artificial Sequence: Nonsense
      sequence

<400> SEQUENCE: 4
acccatagat gcgactggta gacagtgaca cgataggcta atttgatcga tcagtcagcc     60

<210> SEQ ID NO 5
<211> LENGTH: 55
<212> TYPE: DNA
<213> ORGANISM: Artificial Sequence
<220> FEATURE:
<223> OTHER INFORMATION: Description of Artificial Sequence: Nonsense
      sequence

<400> SEQUENCE: 5
cgcatgcaaa agtgatcggg tatcacgcac gtattcttag cagagttatc caacc          55

<210> SEQ ID NO 6
<211> LENGTH: 13
<212> TYPE: DNA
<213> ORGANISM: Artificial Sequence
<220> FEATURE:
<223> OTHER INFORMATION: Description of Artificial Sequence: nonsense
      sequence

<400> SEQUENCE: 6
```

```
gcttgtctag tca                                                              13

<210> SEQ ID NO 7
<211> LENGTH: 13
<212> TYPE: DNA
<213> ORGANISM: Artificial Sequence
<220> FEATURE:
<223> OTHER INFORMATION: Description of Artificial Sequence: nonsense
      sequence

<400> SEQUENCE: 7
gcttgtctat tac                                                              13

<210> SEQ ID NO 8
<211> LENGTH: 13
<212> TYPE: DNA
<213> ORGANISM: Artificial Sequence
<220> FEATURE:
<223> OTHER INFORMATION: Description of Artificial Sequence: nonsense
      sequence

<400> SEQUENCE: 8
gcttgtctag aat                                                              13

<210> SEQ ID NO 9
<211> LENGTH: 44
<212> TYPE: DNA
<213> ORGANISM: Artificial Sequence
<220> FEATURE:
<223> OTHER INFORMATION: Description of Artificial Sequence: nonsense
      sequence

<400> SEQUENCE: 9
taggctaggc cccatatgct gacggcgcat ttgacccaa agtc                             44

<210> SEQ ID NO 10
<211> LENGTH: 41
<212> TYPE: DNA
<213> ORGANISM: Artificial Sequence
<220> FEATURE:
<223> OTHER INFORMATION: Description of Artificial Sequence: nonsense
      sequence

<400> SEQUENCE: 10
gattggggac cagcaccacc ttagcaggat tgacacgggt a                               41

<210> SEQ ID NO 11
<211> LENGTH: 48
<212> TYPE: DNA
<213> ORGANISM: Artificial Sequence
<220> FEATURE:
<223> OTHER INFORMATION: Description of Artificial Sequence: nonsense
      sequence

<400> SEQUENCE: 11
ttaggatcgc gagcttatcc agagtcgacc ggtagggcta cacacaag                        48
```

DNA SEQUENCE ASSEMBLY SYSTEM

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

Developments in the field of genetics and molecular biology have led to a concerted scientific effort to determine the entire DNA sequence of whole organisms. Scientists have already sequenced the complete genome of several microorganisms, and genome sequencing efforts are now turning to larger organisms leading inevitably to determining the complete DNA sequence of human beings. The current biochemical methods used to ascertain the sequence of DNA molecules typically are performed on small segments of DNA due to practical constraints in those processes. While it is theoretically possible to sequence a large DNA molecule by sequencing small pieces systematically beginning at one end of the large piece and proceeding to the other end, there are pragmatic reasons why such a process is difficult. Instead, most current techniques rely on breaking large DNA fragments into small fragments which are then individually sequenced. This is done in a redundant or overlapping procedure in a way that maximizes the likelihood that all the portions of the larger DNA fragments are sequenced one or more times by the sequencing of the overlapping small fragments. This process results in a logic, or computational, problem in that the sequences of the small fragments must be assembled or aligned into larger pieces, which larger pieces are then assembled into still larger pieces in order to create the entire DNA sequence of the large fragment sought to be sequenced.

DNA is a biochemical polymer made up of monomers referred to as "bases" which are conventionally represented by one of four letters, A, T, C, or G. As used herein the small piece of DNA which is subjected to actual biochemical analysis to determine its base sequence is referred to as a "fragment," and the data representing the DNA sequence generated from each fragment is referred to as a "fragment read." Again, in the overall sequencing process, fragment reads are created which are redundant or overlapping to cover most or all sections of the larger DNA piece from which the overlapping were created. The fragment reads must be aligned into one or more contiguous larger segments, such a larger segment being referred to here as a "contig." The overall layout of fragments into contigs is used to determine the sequence of large fragments of DNA. This process is referred to here as "fragment assembly."

Because DNA is a polymer, it is common to refer to DNA pieces using the nomenclature of polymers. Hence, the terminology "mer" is used to refer here to a sequence of bases in a fragment read. In the conventional terminology used, "mer" refers to a sequence of any length and, when prefixed with the number, is used to refer to a sequence of defined length. Thus a 20-mer is a portion of DNA 20 bases in length.

The length of fragment reads and the complexity of problems inherent in assembling the fragment reads into contigs depends on the length of the overall DNA being sequenced and the molecular biology strategy adopted for sequencing that piece of DNA. DNA fragments or pieces are typically inserted into biological carriers, referred to as vectors, and different classes of vectors can host different length DNA fragments. For larger genomes, for example, a popular DNA sequencing strategy involves cloning DNA fragments in excess of 100 kilobases (kb) from one or more chromosomes into so-called BAC vectors, shotgun-cloning at random smaller DNA fragments from the inserts in the BAC vectors, and then sequencing the smaller fragments. The smaller fragments are sequenced to make the fragment reads. The fragment reads must be reconstituted into "contigs," which represent the sequence of the larger BAC inserts, following which the BAC contigs must be arranged according to their positions on the chromosomes. There are a variety of strategies for assembling of the larger genome sequence from these larger contigs, for example, optical mapping.

It should be appreciated that the sequencing strategies can be different, and the problems in using such strategies can be much different in severity depending on the size of the genome which is sought to be sequenced. The whole genome of some smaller organisms, such as for example, the bacterium E. coli, has been entirely derived by random shotgun cloning of small inserts from the whole genome, and then assembling overlaps among the fragment reads in an exhaustive procedure to assemble the pieces into the whole genome. This strategy is feasible where the genome of the organism is small. The genome of an E. coli organism is approximately 4.7 megabases. This approach becomes more untenable when dealing with larger genome sizes. For example, the genome of humans approximates three billion bases. The adoption of a similar assembly method on a genome of this size presents forbidding practical assembly problems.

Significant effort has been undertaken toward software methods that can efficiently handle large amounts of DNA sequence data. Such methods will differ, however, in the efficiency with which they can process the DNA fragment reads into contigs or whole genomic information. The speed with which such algorithms operate is dependent, of course, principally on the number of fragment reads, referred to here by the number n. A number of commonly used computer software fragment read assemblers are now available. However, the assemblers now in use commonly have a processing time that is proportional to $n^2$. With such algorithms whose processing time increases with the square of the number of reads, as the number of reads increases, the rate of increase in the computational time necessary for execution increases quadratically. There are at least seven known programs in operation which do sequence assembly, and all of them have a processing time proportional to $n^2$. These packages include the following: The Phred/Phrap Package (Green et al.), The TIGR Assembler (Sutton et al.), GAP (Bonfield et al.), CAP 2 (Huang), The Genome Construction Manager (Lawrence et al.), Bio Image Sequence Assembly Manager (Smith et al.), and SeqMan (Swindell & Plasterer).

Another method that takes time proportional to the square of n (or perhaps the cube of n) uses genetic algorithms to search for possible layouts of fragment reads (Parson and Johnson). At each iteration of processing, a number of possible layouts are considered and evaluated for their likeliness of being correct. Two functions for evaluating the layouts were developed, one with a processing time proportional to n and the other proportional to $n^2$. In the most successful experiments with this method, the number of possible layouts considered is set to be larger than n.

Depending on which evaluation function is used, the overall processing time to run the algorithm is then proportional either to $n^2$ or $n^3$.

For large scale sequencing operations, the use of algorithms whose processing time is dependent on the square of n results in computational time that may become impractically large. As an example, current efforts at the University of Oklahoma focusing on the genome of the organism *Neisseria gonorrhoeae* have resulted in over 22,000 fragment reads. Reportedly, the assembly of those fragment reads takes about four hours using high stringency fragment read assembly parameters using the Phred/Phrap Package on a Spark Ultra work station. Extrapolating based on differences required by processing speed proportional to $n^2$, and assuming fragment read lengths of 500 and a redundancy of two, it would take over three months to assemble fragment reads from one chromosome of the human genome on this platform. In contrast, if a method has a processing time which is proportional to n, if 4 hours were required to assemble 22,000 fragment reads, using the same assumptions, a human chromosome could be theoretically assembled in less than four days.

More powerful computers can shorten the execution time of fragment assembly software, even for approaches which vary in heir execution time in proportion to $n^2$. However, the computational power of the computer cannot shorten that time by enough. As biochemical sequence data acquisition procedures are becoming more rapid, lengthy fragment assembly procedures could create a bottleneck in DNA sequencing. Moreover, it is typically useful to be able to run sequence assembly procedures multiple times in a growing data set created by the sequencing operation. At various times during the sequencing process, it is appropriate to test whether fragment redundancy is approaching the level at which finishing strategies (to cover gaps in the data, for example) should be initiated. Later, when it is determined that coverage of the genome appears adequate, fragment assembly may be run repeatedly to test the effectiveness of assembly using various different assembly criteria. Fast assembly software, running in time proportional to n, would enhance the efficiency of such analysis even for projects based on small genomes or individual clones.

BRIEF SUMMARY OF THE INVENTION

The present invention is summarized in that a method for assembling DNA fragment reads into contiguous DNA segments includes the steps of creating a table of mers of a given size that appear in all of the fragment reads, while simultaneously counting the occurrences of the mers in all of the fragment reads, then, choosing mer tags for each fragment read using mer counts, ensuring that each mer chosen as a mer tag is chosen as a mer tag for every one of the fragment reads in which it occurs and then using the mer tags to align or assemble the fragment reads into contiguous DNA segments.

The present invention is also summarized in a computer system that includes data structures and methods to input and store fragment read information, then count the occurrences of each mer of a given size in all fragment reads, then use the mer counts as the basis for selecting mer tags for each fragment read, then ensure that for each mer chosen as a mer tag that the mer tag is associated with each of the fragment reads in which it occurs, and then assemble all of the fragment reads into contiguous segments based on the alignment of overlapping mer tags.

It is an object of the present invention to provide a method for assembling fragment reads into contiguous DNA segments which has a processing time that increases linearly with the number of fragment reads rather than increasing by the square or cube of the number of fragment reads.

It is a feature of the present invention that it encompasses features to avoid artifacts in DNA fragment assemblies such as natural repeat sequences and thus is robust and capable of dealing with the biological variants inherent in DNA.

Other objects, advantages, and features will become apparent from the following specification when taken in conjunction with the accompanying drawings.

BRIEF DESCRIPTION OF THE SEVERAL VIEWS OF THE DRAWINGS

FIG. 2 illustrates SEQ ID NO:1.

FIG. 3 is an illustrative example using hypothetical data of the need to avoid unidentified overlaps in assembling fragment reads into contigs. FIG. 3 illustrates SEQ ID NO:2.

FIG. 4 is an illustrative example of a method for breaking ties in selecting mer tags for fragment reads. FIG. 4 uses data from SEQ ID NO:2.

FIG. 5 is an illustrative example of a method of choosing mer tags for fragment reads.

FIG. 6 is an illustrative example using hypothetical data of false overlaps with repeats.

FIG. 7 illustrates that fragments may overlap a mer tag region even though the fragment does not appear in the mer tag list. This demonstrates the need to check for pairwise sequence similarity among all overlapping fragments in contigs.

FIG. 8 illustrates the concept of pairwise sequence similarity in a rolling window. FIG. 8 illustrates SEQ ID NO:3 and 4.

FIG. 9 is an example of a method of merging contigs. FIG. 9 illustrates SEQ ID NO:5.

FIG. 11 illustrates an initial mer table for use with the present invention.

FIG. 12 illustrates a mer table list for use within the method of the present invention.

FIG. 13 illustrates a contig list and the layout thereof and the data structure used by the method of the present invention. FIG. 13 uses data from SEQ ID NO:9, 10 and 11.

FIG. 14 illustrates the process of reversing reads when forming contigs from fragment reads.

DETAILED DESCRIPTION OF THE INVENTION

Figures 1, 2:
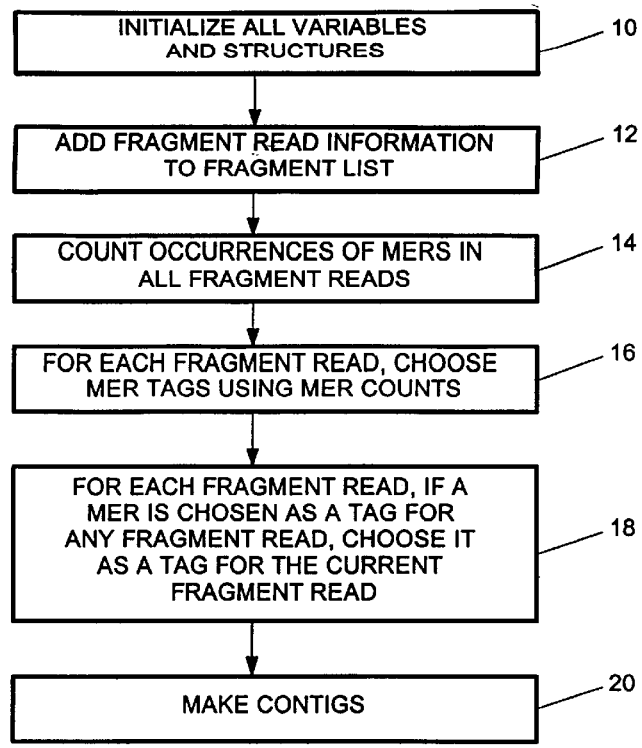
FIG. 1 is an extremely cursory overview in flowchart form of the major portions of the method of the present invention.
FIG. 2 is an illustrative example using hypothetical data of how fragment reads are assembled into contigs.

The flow chart of FIG. 1 is intended to illustrate, in summary form, the main portions of a computer system for assembling DNA sequence information in accordance with the present invention. The objective is to assemble a series of fragment reads into a contiguous DNA sequence, or "contig," using a process in which the processing speed varies in accordance with the number of fragment reads n rather than according to $n^2$ or $n^3$. The method involves multiple passes or scans through the same data set to identify "mers," "mer counts" and then "mer tags." The term "mer" signifies a portion of DNA sequence of pre-defined length. A "mer count" refers to a count of the number of times that a particular mer is found within all of the fragment reads in the data set being analyzed. A "mer tag" refers to specific mers associated with each fragment read, and selected on the basis of mer counts, which are used to assemble the fragment reads.

In the flow chart of FIG. 1, step 10 illustrates that a computer program operating in accordance with this method first initializes all variables and data structures. At step 12 the DNA sequence information contained in all of the fragment reads is entered into the system either manually or electronically and is added to a data structure referred to as a "fragment list." Step 14 is intended to represent the first pass through the data set of fragment reads. During the pass of step 14, the system analyzes each and every mer of user-defined length k in each and every one of the fragment reads in the data set. The result of step 14 is a table of mers in which each mer has assigned to it a number equal to the total number of occurrences of that particular mer in the entire data set. This number of occurrences is the mer count. Thus if k=6, the 6-mer ATGCGA would be associated with a number representing the total number of occurrences of ATGCGA at any position in all of the fragment reads in the data set. If k=6, such data could be collected for all mers of a length of six bases that occur in the data set.

Then, at step 16, a second pass through the data set of fragment reads is conducted. During the pass represented at 16, for each fragment read, the software chooses from among the mers found in each fragment read a number of mers to be used as guides or tags to help align the fragment read with other fragment reads. The chosen mers are referred to as "mer tags." With a provision to eliminate DNA repeat sequences, as will be discussed below, in general the selection of mer tags will be based in part on the position of each mer in the specific fragment read and based on the number of occurrences, or the mer count, for the mer. As this pass through the data set of fragment reads proceeds, adjuncts to the mer table are created, each one associating fragment reads with the mer tags selected so far.

Note that in step 16, mer tags are designated for each fragment read as each fragment read in turn is analyzed. It is quite possible that if a given mer is newly designated as a mer tag during the analysis of one of the fragment reads processed in the pass, that the particular mer designated a mer tag is also contained within one or more fragment reads analyzed earlier in step 16. Therefore, at step 18 another pass through the data set of fragment reads is made. In this pass, for each mer chosen as a mer tag for any fragment read, that same mer is associated as a mer tag for all fragment reads in which it appears. This pass ensures that complete adjunct tables are created associating each mer tag with each fragment read in which it occurs.

The adjuncts to the mer table are then used in step 20 to assemble the fragment reads into contigs. In essence, the occurrence of mer tags in multiple fragment reads will, after checking, specify overlaps between fragment reads that permit the fragment reads to be aligned and assembled into contigs.

FIG. 2 is intended to illustrate this process in its simplest embodiment. Represented at 2A is a DNA sequence in the organism the DNA of which is being sequenced. Sequence 2A, and all other sequences presented in this patent application, are fabricated sequences for purposes of illustration and represent no biological function. The biochemical process of sequencing that DNA has created a series of fragment reads designated 2B, 2C, 2D, 2E, and 2F. The system is first initialized and then the data representing the DNA sequence from those fragment reads is entered into the program to create a fragment list of fragment reads.

The next step is to count occurrences of mers. For purposes of the illustration of FIG. 2, assume that k=6, so a table is made of those 6-mers which occur in the data set and the number of occurrences of each mer is counted. Note that of the $4^6$ possible 6-mers, some mers appear only once (e.g. GCAATG) while others occur more than once (e.g. AGGTTT) and, in this small data set, most occur not at all. Each occurring mer now has associated with it a mer count.

Then, the system scans each fragment read to assign mer tags. For purposes of this simple illustration, let us assign only two mer tags per fragment read (if possible). The system picks as the mer tag for each fragment read the individual mer which has associated with it the lowest mer count provided, of course, that the mer count is at least two. In the illustration of FIG. 2, the chosen mer tags are illustrated by underlined portions of the fragment reads. The mer tags are TATGGC, GGCGTAC, AGGTTT and GGGATT. Then the mer tags are used to logically align the fragment reads, as illustrated at the bottom of FIGS. 2. The consensus sequence of the assembled fragment reads used to make the contig produces the sequence 2A.

The method here is intended to sort through a large number of fragment reads looking for mers of an arbitrary length of length k. While it would be possible to simply create a table of all possible k-mers, to do so would be wasteful of computing resources since a substantial number of the k-mers never occur in a data set. Instead, a k-mer is split into two smaller mers, an x-mer and a y-mer, where k=x+y, an x-mer is the first x bases of a k-mer and a y-mer is the last y bases. A hash table is created that is large enough for all possible x-mers. At each position designed by an x-mer in the hash table, a separate entry is added to store information for each different y-mer that follows the x-mer in a k-mer. Entries for the y-mers are only added for x and y-mers that occur in the data set, so that the table typically has far fewer than $4^k$ entries. An example initial hash table is illustrated in FIG. 11 where x=8. Here each possible 8-mer is encoded using 2 bits per base (i.e., A=00, C=11, G=01, and T=10). The integer value of the encoding of an 8-mer then specifies a particular position in the table. An example hash table is illustrated in FIG. 12 where k=12, x=8, and y=4. (In the processing of actual data, a more typical set of values would be k=24 to 48 and x=8.) In this hash table position, information is stored for three different 12-mers: GCTTGTCTAGTCA (SEQ ID NO:6), GCTTGTCTATTAC (SEQ ID NO:7), and GCTTGTCTAGAAT (SEQ ID NO:8). All are stored within the same position in the hash table since the x-mers (first eight bases) are identical. However, since the y-mers (last 4 bases) are different, each has a separate entry. Contained in each entry is a count of the number of occurrences of the k-mer in the data set. The counts populating the hash table entries are used to determine which mers to use as mer tags to help align the overlaps of fragment reads.

Returning to the mer table created by the system, biology provides another complication to the analysis. In the DNA of most organisms there are naturally repeating sequences, some of which can be significant in length. These naturally repeating mers cannot be used to attempt to define overlaps for assembling fragments, since they occur repetitively throughout the genome, and if used to align adjacent sequences, would prove ambiguous as to which fragments they should align. Therefore, the system must provide a method for attempting to ascertain which of the mers in the hash table are naturally occurring repeat sequences and distinguish those repeats from those sequences which are probably unique to be used in assembly of fragments into contigs.

It is necessary to provide some redundancy in the number of smaller fragments in order to be statistically likely to have read most, preferably all, of the overall DNA being sequenced. In other words, if one is sequencing 1 million bases of DNA, it might be reasonable to break up the 1 million bases into 1,000 fragments of 1,000 bases each. However, if one picked 1,000 random fragments of 1,000 bases each and sequenced them all, one would be statistically unlikely to have sequenced all of the 1 million bases, since it is highly likely that the 1,000 base fragments sequenced would overlap each other significantly. Accordingly, using this sort of shot gin approach, it is appropriate to have an expected redundancy. The expected redundancy value for any given sequencing operation is the average coverage for the entire sequencing operation, defined by the sum of all of the lengths of all of the fragment reads divided by the entire sequence length. The expected redundancy must be considered in the process of identifying natural repeats in the overall sequence.

The purpose of the mer table is to determine which non-repeat k-mers occur in multiple fragment reads so that those k-mers can then be designated mer tags and used to assemble the fragment reads into contigs. Before they can be used, however, it is necessary to negate the possibility that any given k-mer is a natural repeat. This is done by specifying a threshold that specifies the maximum number of the mer count for a mer. When that threshold number of occurrences is surpassed for a given mer, that specific mer is then marked as a repeat. Repeats may not then be used thereafter in assembly of fragment reads into contigs. The premise is that if the number of occurrences or mer count for a mer is significantly above expected, the mer is likely to be a repeat. The expected number of occurrences of any mer is simply the expected redundancy as defined previously. The goal is to identify mers that are unique in the overall biological sequence but present in two or more fragment reads, so that they may be used to define an overlap between fragment reads.

As stated in the summary above, during the second pass through the fragment reads, the mer counts are used to select mer tags for each fragment read. In this scan, an initial set of mer tags is selected for each fragment read. Theoretically any number of mer tags can be chosen for each individual read, but the need for completeness must be balanced with the need for efficiency. If too few mer tags are chosen, there is a risk that overlaps between fragment reads can be missed. If more mer tags than necessary are chosen, storage and processing time are wasted. One answer to the dilemma is to choose two mer tags per read, one located at each end of the fragment read. If the biological data from the sequencing operation is perfect, the selection of two mer tags per read would be quite sufficient. However, given the currently available techniques in the biochemical processes of DNA sequencing, data near the ends of fragment reads tends to be more error prone than data in the middle. Sequencing defects or artifacts created by such errors can cause overlaps to be missed using a scheme in which only two mer tags per fragment read are selected. In practice, it has been found that choosing three to five mer tags per fragment read is the appropriate number to balance the need, for completeness with efficiency, yielding relatively strong completeness without sacrificing significant efficiency. It is appropriate that two of the mer tags for each fragment read be located near the ends of the fragment read with the other mer tags being distributed in between them.

FIG. 3 illustrates some of the problems occurring in selecting the various number of mer tags per fragment reads. Again at the top is represented a DNA sequence designated by the reference number 3A, from which four fragments have been created with fragment reads designated 3B, 3C, 3D and 3E. In FIG. 3, mer tags chosen initially are single underlined and their matches are double underlined. An analysis of the fragment reads 3B, 3C, 3D and 3E based on the use of 6-mers in the mer table has lead to the selection of a single 6-mer mer tag in the center of each read. The 6-mers located near the center of the fragment reads 3B and 3C identify the overlap between fragment reads 3B and 3C and permit the alignment of those two fragments as shown at 3F in FIG. 3. Similarly, the selection of 6-mers at the center of fragments 3D and 3E has led to their alignment as shown at 3G in FIG. 3. However, by failing to choose any 6-mer tags near the ends of each fragment read, the overlap between fragment reads 3C and 3D has been missed. The illustration 3H shows the fragment reads as they could be aligned with use of another mer tag for each fragment read.

Consider the other possibility in which mer tags are chosen for either end of each fragment read (when possible). One might suppose that the mer tags would then identify all read overlaps. However, as illustrated in FIG. 3, this method is prone to error if there are base identification errors in the sequence itself. Note the aligned fragment reads 3B and 3C1 in FIG. 3 that an error has been introduced into the sequence in fragment read 3C1 six bases from the end. That error prevents the discovery of its overlap with fragment reads 3D and 3E and leads to a similar situation as with mer tags in the middle of each fragment read are selected, i.e., the fragment reads cannot be assembled. It is for this reason that the selection of mer tags both at the ends of each fragment read, and distributed in the middle, becomes appropriate.

There is a preferred method for selecting mer tags. As the second scan through the fragment reads is conducted, each fragment read is partitioned into a number of partitions equal to the specified number of mer tags per read. Then, if possible, a specific mer tag is chosen in each of these partitions. A simple criterion may be used to choose a mer tag. The preferred mer tag is that mer in the partition which has the lowest mer count, or the fewest number of occurrences, for all the possible mer tags within the partition. However, the mer count associated with the mer tag must be at least two, if the mer tag is going to be useful to identify overlapping fragments. Obviously if the mer count is one, the mer is unique in the data set and will not define an overlap. Again, the premise is that the fewer number of occurrences, the more likely that the mer tag is unique in a given large DNA fragment or genome, and that the occurrence of that mer in two or more fragment reads indicates a true overlap.

Often there are ties in the mer counts of putative mer tags and the choice of mer tag is therefore dependent upon the partition that is being processed. Ideally it is preferred that mer tags be chosen that are either at the end of the fragment read and spaced evenly throughout the rest of the read. Given this preference, if one is choosing a mer tag for the first partition, one would choose the first mer with the fewest number of occurrences. Conversely, if one is choosing a mer tag for the last partition, one would choose the last mer with the fewest occurrences. For partitions in the middle, it is appropriate to choose as the mer tag a mer with the fewest occurrences that is nearest the center of the partition. FIG. 4 is intended to illustrate some of the rules utilized for breaking ties in a partition.

In FIG. 4, the DNA sequence represented is designated 4A. The fragment reads are 4B, 4C, 4D and 4E. In this example, k=8 and we wish to choose three mer tags per fragment read. To pick mer tags for fragment read 4B, the fragment read is first partitioned into three segments. In the first partition, a mer tag cannot be chosen among the first four mers since the first four mers only occur once each, and hence cannot represent an overlap. The number of occurrences of each 8-mer is indicated underneath its first base, and the partitions are indicated at 4F. The first mer tag chosen in that partition is the first with two occurrences. In the middle partition, we would choose the mer with two occurrences in the center of the partition. In the last partition, the last mer with a mer count of three is chosen. Each mer tag is shown underlined.

The third pass through the data set of fragment reads is conducted so as to determine that if a mer was chosen as a mer tag for any one fragment read within the data set, that same mer is also chosen as a mer tag for all other fragment reads containing that particular mer in the data set. Doing this permits all fragment reads that contain the same mer tag to be placed in the same contig. This step is necessary in order to ensure that fragment reads analyzed earlier in the second scan through the data are not ignored during the contig assembly. The necessity for this step is illustrated in FIG. 5.

In FIG. 5, the DNA sequence represented is 5A which is made up of regions designated X, A, B, C, and Y. Regions A, B and C represent mer tags that will be selected some time during the second and third passes through the fragment read data. In this example 8-mers are selected, and we wish to choose at least two mer tags per fragment read. Mer tags chosen during the second pass are single underlined while those chosen during the third pass through the fragment reads are indicated by double underlines. The fragment reads are 5B, 5C, and 5D. Illustrated at 5E are the results of the first pass to identify mer tags. No mer tag is chosen for the first half of 5B since the X region occurs only once. Note that no overlaps are identified at this point between 5B and 5C. Then, during the third pass, the overlapping mer tags between 5B and 5C are identified and aligned in 5F.

The amount of storage and processing time can be reduced by incorporating a check for previously chosen mer tags while the second scan is being performed. In the second scan, if a mer in the current partition has been previously chosen as a mer tag, the mer can immediately be chosen as a mer tag for the current fragment read. However, checking for previously chosen mer tags during the conducting of the second scan does not eliminate the need for the third scan because, again, mers chosen as a mer tag during latter points of the data set can still be found in fragment reads analyzed earlier during the scan.

By the end of the third scan through the data set of fragment reads, a list of mers chosen as mer tags for individual fragment reads has been created. Associated with each mer tag is a corresponding list of all fragment reads that contain the particular mer tag. This is the information that is now used to determine the layout of fragment reads into contigs.

To form the actual contigs, an iteration is conducted through the list of chosen mer tags. Obviously, if all of the fragment reads in any mer tag list are already in the same contig, the list may be ignored. If the fragment reads are not yet in the same contig, then a check is made to see if the fragment reads in the list have above threshold pair wise sequence similarity in all overlapping regions. If this test: is passed, then all the fragments in the list are overlapped in the same contig. The sequence similarity check merits greater amplification.

A check is conducted for sequence overlap similarity between all fragment reads in the list, including portions of the fragment reads outside of the identified mer tags. If any of the fragments in the list are already contained in a contig, the pair wise sequence similarity of all fragments in the contig is compared with any overlapping fragments in the list. The fragments in a contig may or may not contain the current mer under analysis but might still overlap some of the fragment reads in the current list. A threshold is set that specifies the required amount of sequence match similarity. This threshold should be high, usually at least 80%. If the similarity among reads in a list falls below the threshold, the mer should be marked as a repeat and not used to align overlaps. FIG. 6 illustrates the necessity for performing this step.

In the illustration of FIG. 6 the DNA sequence represented is designated 6A and there is a series of fragment reads designated 6B, 6C, 6D and 6E. Regions of the fragments are designated by the letters A, B, C and D. Note that the region of the sequence identified as BBBBBBBB is a repeated sequence within the sequence above at 6A. When we align the BBBBBBBB mer tag for the four reads, in the absence of a check for pair wise overlap similarity, that mer might be used erroneously for contig assembly. However, when we align the BBBBBBBB mer tags for each of the four fragment reads as done at 6F in FIG. 6, and check the sequence similarity of overlaps, we find that the four reads do not match and should not be aligned on the basis of using the BBBBBBBB mer tag for contig assembly.

FIG. 7 presents an example illustrating the need to check for pairwise sequence similarity among all overlapping fragments in contigs even if they do not contain the current mer tag. In this case the DNA sequence represented is 7A and the four fragment reads are designated 7B, 7C, 7D and 7E. Again the regions of the fragment are designated by the letters A, B, C, D and E and there is a repeat of the region BBBBBBBB. In fragment read 7B the first region BBBBBBBB contains a sequencing error in which the fourth base in the region has been read incorrectly. The result of this error is that fragment read 7B does not occur in the fragment read list associated with a mer tag BBBBBBBB. In the process as described herein, first the candidacy to form a new contig using fragment reads 7B and 7C is considered based on the mer tag AAAAAAAA as shown at 7F. The overlap similarity is good and a new contig containing 7B and 7C is made. Meanwhile the fragment reads 7D and 7E are considered for overlapping in a new contig based on the mer tag DDDDDDDD as shown at 7G. Again, the overlap similarity is good and 7D and 7E are placed in a second new contig. Then when the merging of the two contigs is considered while processing mer tag BBBBBBBB, the overlap similarity of 7B with 7D and 7E must be considered even though 7B does not contain the current mer tag (sufficient sequence similarity of 7B and 7C has already been established). It is noted that there is poor overlap similarity and the two contigs are not merged. If merges were conducted blindly without checking pairwise sequence similarity in overlapping regions, there is a risk of incorrect alignment of fragments. However, the stringency of the comparison for pair wise sequence similarity should be below 100% to permit occasional sequencing errors while still correctly assembling the fragment reads into contigs.

The best way to perform this check for pair wise sequence similarity is by means of a rolling window over the region of overlap. This is done to ensure that an extremely good match in one region does not compensate for a poor match in another region. FIG. 8 illustrates this problem. In FIG. 8 two fragment reads 8A and 8B are being aligned and the x indicates sequence mismatches. The overall similarity is actually good at 82% (49 out of 60) which would exceed an 80% threshold. However, if each of the reads contains good data and correct sequence information, the first portion of the read is probably a repeat and it is clear that the fragments should not be aligned and assembled into a contig. By building a rolling similarity check with a window of size 20, we would find that the last twelve windows have similarities ranging from 45% to 75% which would fall below an 80% threshold. This would result in marking the mer as a repeat, which would be the appropriate outcome in this instance.

Depending on the needs of the user even more sophisticated methods for checking overlaps can be employed. These methods allow fragments to be aligned in a contig even if there is poor data or DNA sequence from the host vectors on the ends of a fragment read. Poor data can be ignored by setting a length at the end of the fragment in which the similarity does not have to meet the match threshold. Portions of the vectors from the host can be longer in length than poor data and are identified by counting the number of reads that mismatch other reads. If only one read mismatches, one can make the assumption that the mismatched region is unremoved vector. If more than one read mismatches or the length of the mismatch is longer than reasonable, a repeat is assumed. The desirability of these methods is strongly dependent on the type, amount, and quality of data available.

If the pair wise sequence similarity of all fragment reads in a mer tag list are above threshold, then all fragment reads in the list are placed in the same contig. This is accomplished in the following manner. If none has yet been assigned to a contig, a new contig is made and all other reads are added to it. If at least one fragment is already contained within a contig then the other fragments not yet assigned to a contig are added to it. If another fragment in the list is already in a different contig, the fragment bridges a gap between contigs and the contigs are merged. FIG. 9 illustrates the case where the merge of contigs is indicated.

In FIG. 9 the DNA sequence represented is 9A and the fragment reads are 9B, 9C, 9D, and 9E. A first contig is created using the mer tag AAGTGAT as illustrated at 9F. A second contig is created by overlapping the fragment reads 9D and 9E using the mer tag CACCGACG as shown at 9G. The mer tag GGGTATCA is then used as a basis for merging the two contigs.

At the completion of the iteration through the list of mer tags, a list of contigs has been created. Each contig is represented as a list of information about the fragment reads that are contained within the contig. The information includes an identifier for the fragment read and an offset of the read within the contig.

It has been found that the computational complexity of the preferred implementation of the algorithm described herein is linear with respect to n, n being the number of fragment reads in the data set. The complexity analysis relies on the assumption that there is a practical upper bound to the size of the mer tags that depends neither on the number of fragment reads nor on the length of the actual sequence. We next discuss this assumption that allows us to consider the mer size constant in the analysis.

We define the following symbols:
k size of mer tag
n number of fragment reads
s length of actual sequence
f average length of a fragment read
r average redundancy
m number of mer tags to choose per f bases
t total number of mer tags to choose We state the following:

$$n = \frac{sr}{f}$$

$$s = \frac{nf}{r}$$

$$t = \frac{sm}{f}$$

A mer tag size of k provides $4^k$ possible unique tags. We must have at least as many possible mer tags as the total number of tags we choose. Given this and a series of substitutions we find the following.

$$4^k \geq t$$

$$4^k \geq \frac{sm}{f}$$

$$4^k \geq \frac{nm}{r}$$

$$k \geq \log_4 \frac{nm}{r}$$

$$k \geq \log_4 n + \log_4 m - \log_4 r$$

$$k \geq \log_4 n + \text{constant}$$

At this point, it appears that the size of the mer tag, k, is a function of n, the number of fragments. Although this is true in theory, in practice there is an upper bound to k.

An upper bound of k can be approximated by using a Poisson distribution to estimate the probability that a random k-mer occurs more than once in a sequence (Studier 1989). The probability that a random mer has exactly p occurrences is estimated by $$P(p) = \frac{x^p e^{-x}}{p!} \quad \text{where } x = \frac{s}{4^k}$$

and the probability that a randomly chosen k-mer occurs two or more times is $$P(\leq 2) = 1 - (P(0) + P(1)).$$

When we consider a genome ten times the size of Human and graph the probabilities for various sizes of mers (FIG. 15) we see that the probability of two or more mer occurrences approaches zero near a mer size of 19. Since almost all known genomes are smaller than ten times the size of the human genome, this can be used to estimate a reasonable upper bound on k.

Figures 15, 16:
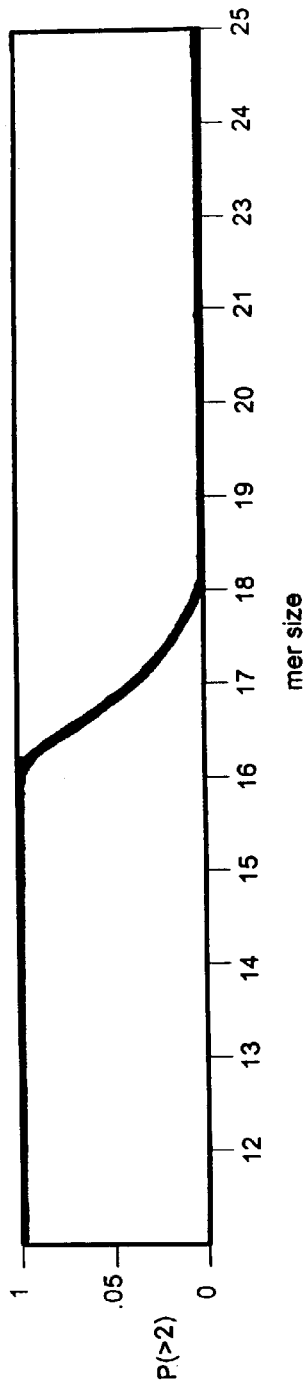
FIG. 15 illustrates a mathematical relationship of mer sizes for large genomes.
FIG. 16 is an illustration of the computational complexity of the method of the present invention.

An absolute upper bound on k is set by the length of fragment reads. At present, although some technologies produce reads in excess of 1000 base pairs, the usable portion is usually about 500 base pairs long. clearly, the mer tag size must be less than this or the algorithm is useless for identifying overlaps. We can state that the absolute upper bound on the mer size is set not by the length of the actual sequence nor of the number of fragment reads, but rather on the length of fragment overlaps. In the degenerate case, the bound is approximately 500. We can therefore consider k, the size of mer tags, to be a constant in our analysis of the complexity of the algorithm. Given this assumption, an analysis of the complexity of individual steps as listed in FIG. 1 and specified in FIG. 16 is provided next.

Step 10 is completed in constant time. The three major data structures used are the hash table for the mers, the list of fragment reads, and the list of contigs. Each of the positions in the hash table is an empty list of mers. The time to accomplish its initialization is therefore constant since the length of the table is dependent upon the size of the mer, which is constant. The fragment read and contig lists are both empty at this point, so the time to clear them is also constant.

In step 12, we read once through each of the fragment read sequences, encoding the sequence and determining its length. This iteration depends on the number of fragments and takes time proportional to n.

Step 14 requires a single read through all of the encoded fragment read sequences, counting occurrences of mers. To read the sequences takes time proportional to n. To count the mers, it is necessary to access the hash table. Indexing the hash table takes place in constant time since we use the first x bases of the mer as the index. The number of entries at each position in the hash table can be at most $4^y$. Since y is constant, accessing a mer in the list is also constant. The overall complexity of this step is proportional to n.

During each of steps 16 and 18, we again scan through the sequence of each of the fragment reads, accessing the hash table once for each mer that is contained in the sequence. The scans require time proportional to n and accessing the table is constant. In addition, for each new mer tag, we add onto the mer's list of associated fragment reads. We always add to the end of the list, so this step takes constant time. The time complexity for each of steps 16 and 18 is n.

In step 20 we iterate through each of the lists in the hash table of mers, possibly making contigs with each of the fragment lists associated with mer tags. Since the greatest possible number of mer tags that can be chosen is $4^{x+y}$ and x+y is a constant, the number of mer tag lists that must be processed is constant. (Note that the number chosen is actually much less than $4^{x+y}$). Making a contig with each of the mer tag lists is also constant. Recall that we set a threshold for the maximum count of mer occurrences allowed before a mer is marked as a repeat. This keeps the maximum length of any list at less than the threshold, so the lists are constant in length. Since the lists' lengths are constant, the number of pairwise comparisons required for the similarity check is dependent on a constant. Making a new contig is constant in time and adding to or merging contigs is at most proportional to n. Overall, step 20 completes in time to proportional to n.

Following this portion of the specification is a listing in pseudo code of a detailed embodiment of the method of the present invention. The use of such a pseudo code table will enable those of ordinary skill in the art to embody the method of the present invention in any appropriate computer processing language. Those needing further details about this algorithm in order to specifically implement the method of this invention in a specific language may make reference to this pseudo code table, although reference to this pseudo code is not required to understand the method of the present invention. Additional complexities and intricacies of the method of the present invention will also become apparent from a review of the pseudo code table as is well within the knowledge of those of ordinary skill in the art.

Figure 10:
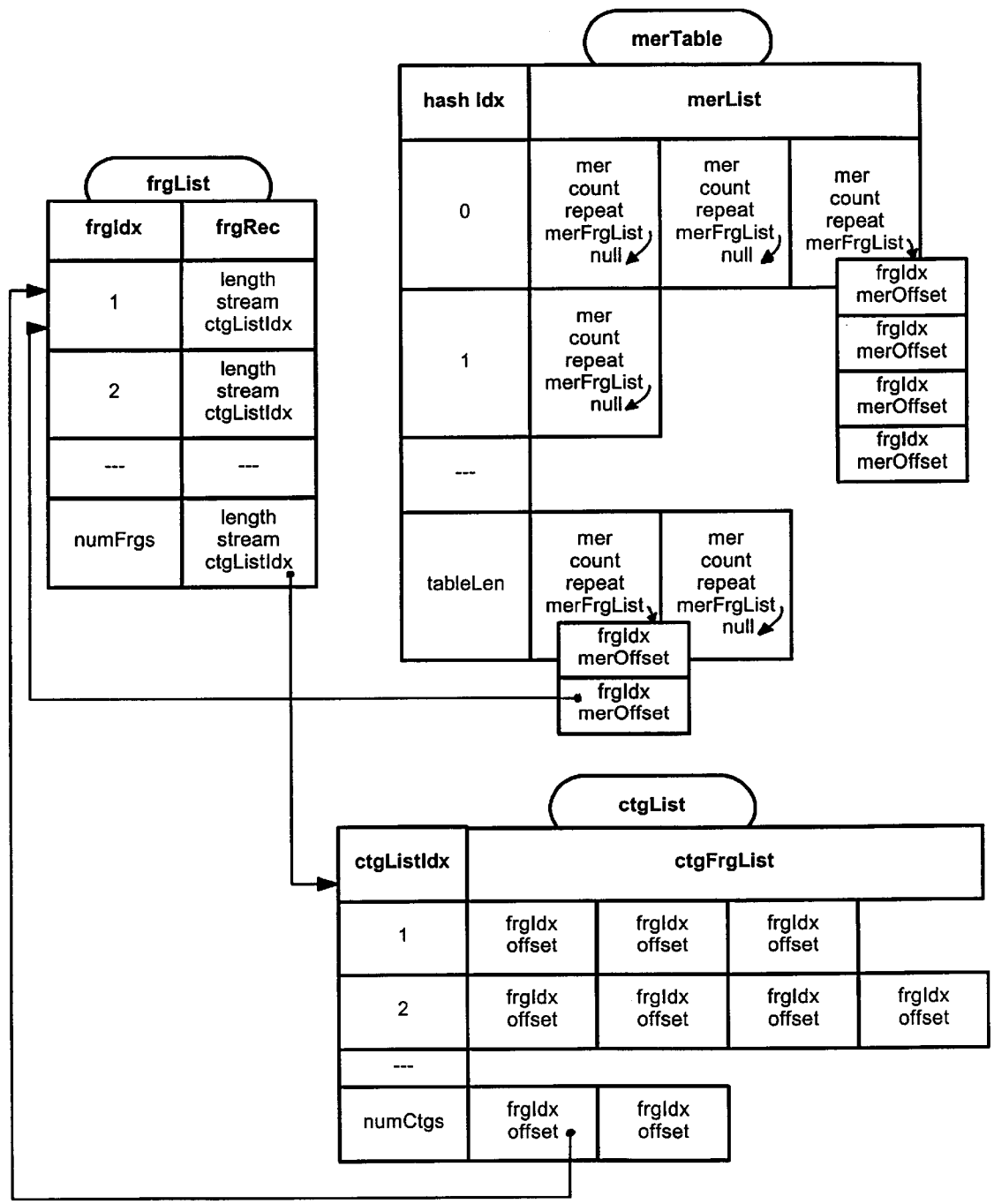
FIG. 10 illustrates data structures used by the system of the present invention.

FIG. 10 illustrates the data structures for the data used in the pseudo code example which follows. In the example of FIG. 10 the frgList contains FrgRec for each fragment read in the data set. In a FrgRec, ctgListIdx is an index into the ctgList, which is the list of all contigs being made. The merTable is a hash table. The first x bases of a mer are used to index into the table and the last y bases of a mer are contained in the MerRec records in the merList. Each MerRec whose mer has been chosen as a mer tag has a merFrgList associated with it. A merFrgList is a list of MerFrgRec. In a MerFrgRec, the frgIdx is an index of a fragment read record which is contained in the frgList. The merOffset is the offset of a particular mer in the fragment read. The ctgList is a list of all contigs so far in the data set. Each contig is represented by a list of CtgFrgRec. The frgIdx in a CtgFrgRec indexes a FrgRec in the frgList. The offset specifies the position of the fragment read in the contig under assembly.

FIG. 11 illustrates an initial mer table. In this example the length of the mers, k=12, while the length of the first section of the mers, x=8, and the length of the table is 65,536. The integer values of the 2 bit encoding of the 8-mers indexes the table.

FIG. 12 illustrates a mer table list. In this example consider the following three mers in the case where x=8 and y=4: GCTTGCTAGTCA, GCTTGCTATTAC, and GCTTGCTAGAAT. The first. x bases are identical for each of the three mers so all hash into the merTable at position 31,352. The last y bases are different, so each mer has its own record in the merRecList. In the data set of fragment reads for this example, we have so far encountered one mer of GCTTGCTAGTCA, six mers of GCTTGCTATTAC, and three examples of the mer GCTTGCTAGAAT.

FIG. 13 is an illustration of the layout of the ctgList. In this example sixteen fragment reads are in the data set, twelve reads having been aligned into three contigs. Each ctgFrgList contains a ctgFrgRec that includes the frgidx (an index into the frgList) for each fragment read in the contig. The records also include the offset of the read in the individual contig under assembly. Four fragment reads (frgIdx=4, 8, 9, and 11) did not overlap into any other read and they are not therefore not assembled into any contig. The fragment reads for each contig are aligned according to the offsets listed in the ctgFrgRec.

FIG. 14 illustrates the fact that reversing reads may be appropriate when forming contigs. The example shows three fragment reads added together one at a time to a growing contig. The mer occurs in the reverse direction in the third fragment so the offset from the original 3' end of the read is determined and used.

| Name | Type | | Description |
|---|---|---|---|
| | Type Definitions | | |
| StreamT | string | | Base call sequence, encoded with 2 bits per base (A = 00, C = 11, G = 01, T = 10) |
| MerT | StreamT | | Encoded mer |
| FrgRec | Record | | Fragment read information |
| | int | length | Read length |

-continued

| | | | |
|---|---|---|---|
| | StreamT | stream | Base call sequence of read |
| | int | ctgListIdx | Index in a CtgListT |
| | End | | |
| FrgListT | FrgRec List | | List of FrgRec |
| MerFrgRec | Record | | Information on a fragment read that contains a given mer |
| | int | frgIdx | Index of a FrgRec in a FrgListT |
| | int | merOffset | Offset of mer in a FrgRec stream |
| | End | | |
| MerFrgListT | MerFrgRec List | | List of MerFrgRec |
| MerRec | Record | | Mer information |
| | MerT | mer | Encoded last y bases of mer |
| | int | count | Count of mer occurrences in all fragment reads |
| | Boolean | repeat | True if the mer is a putative repeat |
| | MerFrgListT | merFrgList | List of MerFrgRec |
| | End | | |
| MerListT | MerRec List | | List of MerRec |
| MerTable T | MerListT List | | Hash table of mers, hashed on first x bases in mer, chained by last y bases in mer, chains are of type MerListT |
| ScoreRec | Record | | Score information |
| | MerT | mer | Mer |
| | int | merOffset | Offset of mer in a FrgRec stream |
| | int | score | Mer score |
| | End | | |
| CtgFrgRec | Record | | Information on a fragment read that is in a contig |
| | int | frgIdx | Index of a fragment read in a FrgListT |
| | int | offset | Offset of fragment read in a contig |
| | End | | |
| CtgFrgListT | CtgFrgRec List | | List of CtgFrgRec, ordered by offset |
| CtgListT | CtgFrgListT | List | List of CtgFrgListT, one ctgFrgList per contig |

Variables and Data Structures

| | | |
|---|---|---|
| newCtgFrg | CtgFrgRec | New CtgFrgRec |
| ctgList | CtgListT | List of contigs |
| ctgListIdx | int | Current index of a contig in a CtgListT |
| found | Boolean | True if found |
| frgList | FrgListT | List of FrgListRec for fragment reads in the dataset |
| frgRec | FrgRec | Current FrgRec |
| maxCount | int | Count threshold for the number of occurrences of a mer in the dataset |
| mer | MerT | Current mer |
| newMerFrg | MerFrgRec | New MerFrgRec |
| merFrgRec | MerFrgRec | Current MerFrgRec |
| merRec | MerRec | Current MerRec |
| merTable | MerTableT | Hash table of all mers of length x + y that occur in the dataset |
| numFrgs | int | Number of fragment reads in frgList |
| numMers | int | Number of mer tags to choose for each fragment read |
| merOffset | int | Offset of a mer in a fragment read |
| scoreRec | ScoreRec | Current ScoreRec |
| tagScoreRec | ScoreRec | ScoreRec of highest scoring mer for current partition |

FIG. 10 charts the three main data structures (frgList, merTable, and ctgList) and their relationships.

| Prototype | Returns | Description |
|---|---|---|
| Functions | | |
| addToList (List, Item) | List | Adds Item to List |
| assignScore (MerT, int) | ScoreRec | Assigns score for MerT |
| betterScore (ScoreRec, ScoreRec, int) | Boolean | Returns true if 1st ScoreRec is better than 2nd for given partition |
| getCtgListIdx (MerFrgListT) | int | Returns index of any contig in the list, 0 if none |
| getMerRec (MerTableT, MerT) | MerRec | Returns MerRec for MerT from MerTableT |
| getNextFrgRead ( ) | FrgRec | Returns next fragment read, stored in a FrgRec |
| getNextMer (FrgRec, int) | MerT | Returns next mer from FrgRec for current partition; if int is 0, partition is entire 5' to 3' read |
| inMerFrgList (MerFrgListT, int) | Boolean | Returns true if the read indexed by int is in MerFrgListT |
| listLen (List) | int | Returns length of List |
| overlapOK (MerFrgListT) | Boolean | Returns true if all pair wise match similarities are above threshold |
| mergectgs (CtgListT, int, int) | CtgListT | Merges contigs indexed by the two int |
| newctgFrgRec (CtgFrgListT, int) | CtgFrgRec | Makes a new CtgFrgRec |
| newCtg (CtgListT, int) | int | Makes a new contig, returns its index in a CtgListT |
| newMerFrgRec (int, int) | MerFrgRec | Makes a new MerFrgRec |
| oneCtg (MerFrgListT) | Boolean | Returns true if all in the MerFrgListT are in the same contig |

We claim:

1. A method for automated assembly of DNA sequence data consisting of DNA fragment reads into contiguous DNA segments using a digital computer with processing and information storage capabilities, the method comprising the steps of:

entering into the computer storage information representing the DNA sequence data from a plurality of DNA fragment reads;

scanning the fragment reads to count each occurrence of each possible mer of length k to create a mer table, the mer table including a mer count for each mer representing the total number of occurrences of that mer in all of the fragment reads;

scanning the fragment reads to pick from the mers occurring in each fragment read at least one mer tag, and associating with each mer tag each fragment read in which the mer tag occurs; and using the mer tags to assemble the fragment reads into contiguous segments of DNA sequence.

2. A method as claimed in claim 1 wherein the step of scanning the fragment reads to pick mer tags comprises scanning the fragment reads two times, a first time to identify at least one mer tag for each fragment read and a second time to associate with each mer tag each fragment read in which the mer occurs.

3. A method as claimed in claim 1 wherein the mers are picked as mer tags based on the lowest mer count associated with the mers as long as the mer count is at least 2.

4. A method as claimed in claim 1 further comprising marking as a repeat any mer the mer count for which exceeds a user-defined threshold number.

5. A method as claimed in claim 1 wherein the value k for the length of the mers is a user-selected parameter.

6. A method as claimed in claim 1 where during the step of scanning the fragment reads to pick mer tags, dividing each of the fragments reads into partitions and picking at least one mer tag for each partition in each fragment read.

7. A method as claimed in claim 6 wherein there are at least three partitions created for each fragment read and three mer tags picked for each fragment read.

8. A method as claimed in claim 7 wherein the mer tags for partitions at the ends of each fragment read are selected to be near the ends of the fragment reads while mer tags for partitions not at the ends of the fragment read are selected to lie near the middle of the partition.

9. A method as claimed in claim 1 wherein the step of using the mer tags to assemble the fragment reads into contiguous segments of DNA sequence includes performing a pairwise sequence comparison in all overlapping regions of fragment reads.

10. A method for automated assembly of DNA sequence data consisting of DNA fragment reads into contiguous DNA segments using a digital computer with processing and information storage capabilities, the method comprising the steps of:

entering into the computer storage information representing the DNA sequence data from a plurality of DNA fragment reads;

scanning the fragment reads to count each occurrence of each possible mer of length k to create a mer table, the mer table including a mer count for each mer representing the total number of occurrences of that mer in all of the fragment reads;

scanning the fragment reads to pick from the mers occurring in each fragment read at least one mer tag, and associating with each mer tag each fragment read in which the mer tag occurs; and using the mer tags to assemble the fragment reads into contiguous segments of DNA sequence the step of using the mer tags to assemble the fragment reads into contiguous segments of DNA sequence including performing a pairwise sequence comparison on a rolling window of DNA sequence in the fragment reads to be assembled and not assembling the fragment reads into contiguous segments if the pairwise sequence comparison shows less that a user defined level of sequence identity.

11. A data processing system for assembling DNA sequence information from DNA fragment reads into contigs of contiguous DNA sequence, the system comprising a digital computer and associated data storage devices, the digital computer programmed to perform the following steps:

entering into the data storage devices of the computer information representing the DNA sequence from a plurality of fragment reads;

scanning the fragment reads to count each occurrence of each possible mer of length k to create a mer table with a mer count for each mer representing the total number of occurrences of that mer in all of the fragment reads;

scanning the fragment reads to pick from the mers occurring in each fragment read at least one mer tag, associating with each mer tag each fragment read in which the mer tag occurs; and using the mer tags to assemble the fragment reads into contigs.

12. A system as claimed in claim 11 wherein the step of scanning the fragment reads to pick mer tags comprises scanning the fragment reads two times, a first time to identify at least one mer tag for each fragment read and a second time to associate with each mer tag each fragment read in which the mer occurs.

13. A system as claimed in claim 11 wherein the mers are picked as mer tags based on the lowest mer count associated with the mers as long as the mer count is at least 2.

14. A system as claimed in claim 11 further comprising marking as a repeat any mer the mer count for which exceeds a user-defined threshold number.

15. A system as claimed in claim 11 further comprising during the step of scanning the fragment reads to pick mer tags, dividing each of the fragments reads into partitions and picking at least one mer tag for each partition in each fragment read.

16. A system as claimed in claim 15 wherein there are at least three partitions created for each fragment read and three mer tags picked for each fragment read.

17. A system as claimed in claim 16 wherein the mer tags for partitions at the ends of each fragment read are selected to be near the ends of the fragment reads while mer tags for partitions not at the ends of the fragment read are selected to lie near the middle of the partition.

18. A system as claimed in claim 11 wherein the step of using the mer tags to assemble the fragment reads into contigs includes performing a pairwise sequence comparison in all overlapping regions of fragment reads.

19. A system as claimed in claim 11 wherein the step of using the mer tags to assemble the fragment reads into contigs includes performing a pairwise sequence comparison on a rolling window of DNA sequence in fragment reads to be assembled and not assembling fragment reads into contiguous segments if the pairwise sequence comparison shows less that a user defined level of sequence identity.

* * * * *